United States Patent
Turner

(10) Patent No.: US 11,607,281 B2
(45) Date of Patent: Mar. 21, 2023

(54) DETECTING UNCONTROLLED MOVEMENT

(71) Applicant: INTUITIVE SURGICAL OPERATIONS, INC., Sunnyvale, CA (US)

(72) Inventor: Michael Turner, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 389 days.

(21) Appl. No.: 16/824,575

(22) Filed: Mar. 19, 2020

(65) Prior Publication Data
US 2020/0214778 A1 Jul. 9, 2020

Related U.S. Application Data

(63) Continuation of application No. 15/503,358, filed as application No. PCT/US2015/044590 on Aug. 11, 2015, now Pat. No. 10,646,291.

(Continued)

(51) Int. Cl.
*A61B 34/35* (2016.01)
*A61B 34/37* (2016.01)
(Continued)

(52) U.S. Cl.
CPC .............. *A61B 34/35* (2016.02); *A61B 17/00* (2013.01); *A61B 34/30* (2016.02); *A61B 34/37* (2016.02);
(Continued)

(58) Field of Classification Search
CPC ......... A61B 34/35; A61B 34/30; A61B 34/37; A61B 34/74; A61B 34/75; A61B 17/00; A61B 2017/00075
(Continued)

(56) References Cited

U.S. PATENT DOCUMENTS 5,943,914 A * 8/1999 Morimoto .............. A61B 34/76
414/2
6,035,228 A 3/2000 Yanof et al.
(Continued)

FOREIGN PATENT DOCUMENTS

CN 102612350 A 7/2012
EP 2939633 A1 11/2015
(Continued)

OTHER PUBLICATIONS

Extended European Search Report for Application No. EP15831989.7, dated Feb. 14, 2018, 12 pages.
(Continued)

*Primary Examiner* — Carl H Layno
*Assistant Examiner* — Michael J Lau
(74) *Attorney, Agent, or Firm* — Artegis Law Group, LLP

(57) ABSTRACT

A system includes a manually movable input control configured to generate signals when a movement of one or more mechanical degrees of freedom of the input control is detected and a control module. The control module is configured to determine whether a movement of the input control is anticipated to cause an instrument to move outside of a safe range of movement of the instrument and command the system to switch from an operating mode to a safe mode in response to determining that the movement of the input control is anticipated to cause the instrument to move outside of the safe range of movement of the instrument. The instrument is separate from the input control. In the operating mode the instrument moves in response to movement of the input control. In the safe mode the instrument does not move in response to movement of the input control.

20 Claims, 5 Drawing Sheets

Related U.S. Application Data

(60) Provisional application No. 62/036,298, filed on Aug. 12, 2014.

(51) Int. Cl.
*A61B 34/00* (2016.01)
*A61B 34/30* (2016.01)
*A61B 17/00* (2006.01)

(52) U.S. Cl.
CPC .............. *A61B 34/74* (2016.02); *A61B 34/75* (2016.02); *A61B 2017/00075* (2013.01)

(58) Field of Classification Search
USPC ............................................................ 606/1
See application file for complete search history.

(56) References Cited

U.S. PATENT DOCUMENTS

| | | | |
|---|---|---|---|
| 6,120,433 A | 9/2000 | Mizuno et al. | |
| 6,238,384 B1 | 5/2001 | Peer | |
| 6,364,888 B1* | 4/2002 | Niemeyer | A61B 34/37 348/E13.016 |
| 6,459,926 B1 | 10/2002 | Nowlin et al. | |
| 6,496,756 B1 | 12/2002 | Nishizawa et al. | |
| 6,594,552 B1 | 7/2003 | Nowlin et al. | |
| 7,453,227 B2* | 11/2008 | Prisco | B25J 9/1689 700/254 |
| 7,887,530 B2* | 2/2011 | Zemlok | A61B 17/072 606/1 |
| 8,332,072 B1 | 12/2012 | Schaible et al. | |
| 8,380,126 B1 | 2/2013 | Ma et al. | |
| 8,496,647 B2 | 7/2013 | Blumenkranz et al. | |
| 8,682,489 B2 | 3/2014 | Itkowitz et al. | |
| 8,776,800 B2 | 7/2014 | Skora et al. | |
| 10,646,291 B2 | 5/2020 | Turner | |
| 2004/0106916 A1 | 6/2004 | Quaid et al. | |
| 2004/0243147 A1* | 12/2004 | Lipow | A61B 34/74 606/130 |
| 2004/0243148 A1 | 12/2004 | Wasielewski | |
| 2005/0251110 A1 | 11/2005 | Nixon | |
| 2006/0095143 A1* | 5/2006 | Sunaoshi | B25J 9/1689 700/2 |
| 2007/0013336 A1 | 1/2007 | Nowlin et al. | |
| 2007/0138992 A1* | 6/2007 | Prisco | A61B 34/70 318/568.21 |
| 2007/0142823 A1 | 6/2007 | Prisco et al. | |
| 2007/0142825 A1 | 6/2007 | Prisco et al. | |
| 2007/0282228 A1 | 12/2007 | Einav et al. | |
| 2008/0004633 A1 | 1/2008 | Arata et al. | |
| 2008/0010706 A1 | 1/2008 | Moses et al. | |
| 2008/0188890 A1* | 8/2008 | Weitzner | A61B 1/00154 606/205 |
| 2009/0082661 A1 | 3/2009 | Saladin et al. | |
| 2009/0088774 A1 | 4/2009 | Swarup et al. | |
| 2009/0198104 A1 | 8/2009 | Sugiyama | |
| 2009/0245600 A1 | 10/2009 | Hoffman et al. | |
| 2010/0028254 A1* | 2/2010 | Masuda | B82Y 30/00 423/622 |
| 2010/0160728 A1 | 6/2010 | Yoshie | |
| 2010/0161129 A1 | 6/2010 | Costa et al. | |
| 2010/0228264 A1* | 9/2010 | Robinson | A61B 18/1206 606/130 |
| 2010/0292843 A1* | 11/2010 | Kariyazaki | B25J 9/1676 901/46 |
| 2011/0118748 A1 | 5/2011 | Itkowitz et al. | |
| 2011/0152882 A1 | 6/2011 | Wenderow et al. | |
| 2011/0282493 A1 | 11/2011 | Ortmaier | |
| 2012/0071891 A1* | 3/2012 | Itkowitz | G05B 15/02 715/863 |
| 2012/0120222 A1 | 5/2012 | Lettow et al. | |
| 2012/0184955 A1 | 7/2012 | Pivotto et al. | |
| 2012/0283747 A1 | 11/2012 | Popovic et al. | |
| 2013/0035696 A1* | 2/2013 | Qutub | A61B 34/10 606/130 |
| 2013/0096497 A1* | 4/2013 | Duindam | A61M 25/0133 604/95.01 |
| 2013/0172906 A1* | 7/2013 | Olson | A61B 34/30 606/130 |
| 2014/0052154 A1 | 2/2014 | Griffiths et al. | |
| 2014/0088410 A1 | 3/2014 | Wu | |
| 2014/0158141 A1 | 6/2014 | Winer | |
| 2014/0171778 A1 | 6/2014 | Tsusaka et al. | |
| 2014/0303605 A1 | 10/2014 | Boyden et al. | |
| 2014/0303660 A1 | 10/2014 | Boyden et al. | |
| 2014/0324070 A1 | 10/2014 | Min et al. | |
| 2015/0342689 A1 | 12/2015 | Kamon et al. | |
| 2018/0214223 A1 | 8/2018 | Turner | |

FOREIGN PATENT DOCUMENTS

| | | |
|---|---|---|
| JP | 2014124229 A | 7/2014 |
| WO | WO-0007503 A1 | 2/2000 |
| WO | WO-2006124390 A2 | 11/2006 |
| WO | WO-2011041428 A2 | 4/2011 |
| WO | WO-2011060139 A2 | 5/2011 |
| WO | WO-2011060171 A1 | 5/2011 |
| WO | WO-2014104087 A1 | 7/2014 |
| WO | WO-2016025440 A1 | 2/2016 |

OTHER PUBLICATIONS

International Search Report and Written Opinion for Application No. PCT/US15/44590, dated Nov. 20, 2015, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

DETECTING UNCONTROLLED MOVEMENT

RELATED APPLICATIONS

The present application is a continuation of U.S. patent application Ser. No. 15/503,358 filed Feb. 10, 2017, now U.S. Pat. No. 10,646,291, which is the U.S. national phase of International Application No. PCT/US2015/044590 filed Aug. 11, 2015, which designated the U.S. and claims priority to and the benefit of the filing date of U.S. Provisional Patent Application 62/036,298, entitled "DETECTING UNCONTROLLED MOVEMENT," filed Aug. 12, 2014, each of which is incorporated by reference herein in its entirety.

BACKGROUND

Teleoperated or computer assisted medical systems often employ a master control that a physician or other medical personnel can use to control actuated slave medical instruments. A medical instrument may, for example, include a tool such as a scalpel, forceps, or a cauterizing tool, and a surgeon may operate a master control similar to a joystick to provide control signals to a control system. The control system can then convert the control signals into actuation signals that drive actuators to move the instrument, for example, to cut, clamp, or cauterize a patient's tissue so that the tool movement follows the master control movement. One potential concern for such systems is inadvertent or uncontrolled movement of the master control, because a patient could be injured if uncontrolled movement of the master control causes uncontrolled operation of the tool that interacts with a patient's tissue. Surgeons can be trained to avoid situations where uncontrolled movement is possible, but additional techniques or fail safes may be desirable to prevent uncontrolled movement.

One way to reduce the chance of uncontrolled movement of the master control is to restrict movement of the mechanical components of the master control. For example, a master control may be balanced or actively driven so that gravity does not cause the master control to drift away from any position in which a physician may leave the master control. Other ways to reduce the chance of uncontrolled movement of an instrument may use a "locked" mode that decouples the master control from the instrument, so that in the locked mode, movement of the master control does not cause corresponding movement of the instrument. The locked mode might be automatically activated when a physician is not in the proper position for use of the master control. In particular, the system may default to the locked mode unless sensors detect that a physician is in the proper position for use of the system including, for example, being in position to view any movement of an end effector of the medical instrument. However, after a physician has taken a medical system out of the locked mode, the physician might release a master control while remaining in position to use the medical instrument. Releasing the master control under such circumstances may create the risk of the master control moving without physician input, resulting in uncontrolled motion of the medical instrument. For example, gravity compensation in the master control may be imperfect, or a physician's knee or hand may accidentally bump the master control while the physician is in position to use the instrument and the instrument is not in the locked mode.

SUMMARY

In accordance with an aspect of the invention, a control module or control process for a medical system can evaluate relationships among the control signals for multiple axes of a master control to evaluate relationships among the control signals and detect whether the master control is moving autonomously. When autonomous movement is detected, the medical system may be placed in a locked mode in which movement of the master control is decoupled from movement of an instrument or in which one or more axes of the master control are locked in their current positions. Autonomous movement detection could also provide a secondary mitigation of system failures, such as a broken master control counterbalance or an erroneous master control or tool position sensor, that could pull the master out of a physician's hand if the primary system failure mitigations do not detect the failure quickly.

One specific embodiment of the invention is a teleoperated medical system that uses robotic technology. The system may include a component such as a component of a master device or of a slave device that may be configured for manual manipulation. The device generates signals indicating movement of multiple degrees of freedom of movement of the component. A detection module can be configured to analyze the signals from the component and to detect uncontrolled movement based on that analysis. When uncontrolled movement is detected, the system to switch from an operating mode to a safe mode in response to detection of uncontrolled movement of the component.

Another specific embodiment of the invention is a method for controlling a teleoperated medical system. The method may include: measuring multiple degrees of freedom of a component of the robotic medical system while the component is configured for manual movement; analyzing movements of the degrees of freedom to identify uncontrolled movement of the component; and switching the robotic medical system to a safe mode in response to unsafe uncontrolled movement being detected.

DETAILED DESCRIPTION

A control system or process for interpreting manual manipulations of a multi jointed component of a medical system can monitor independent movements in the joints to distinguish movement of the component that is likely to be user-controlled from movement of the component that is likely to be uncontrolled. For example, each of the joints or mechanical degrees of freedom of a master control for a teleoperated medical system may be categorized as either a gravity joint or a non-gravity joint. A gravity joint may be a joint such that the force of gravity might cause that joint to move if that movement is not opposed, for example, by a physician's hand. A non-gravity joint may be a joint such that the force of gravity will not cause the joint to move. Most joints in a master control may be gravity joints, but some joints, such as the joints that control tool roll or tool grip, may be non-gravity joints. Under normal operation, a user manually manipulating a master control or other multi-jointed component of a medical system may cause movement of all joints. However, if only the gravity joints move without motion of the non-gravity joints, a control system or process may determine that the component is moving in response to gravity and without user guidance. Other types of uncontrolled movement, for example, movement caused by an accidental bumping of a multi-jointed component, may be similarly detected using more complex relationships between the movements of the joints.

Figure 1:
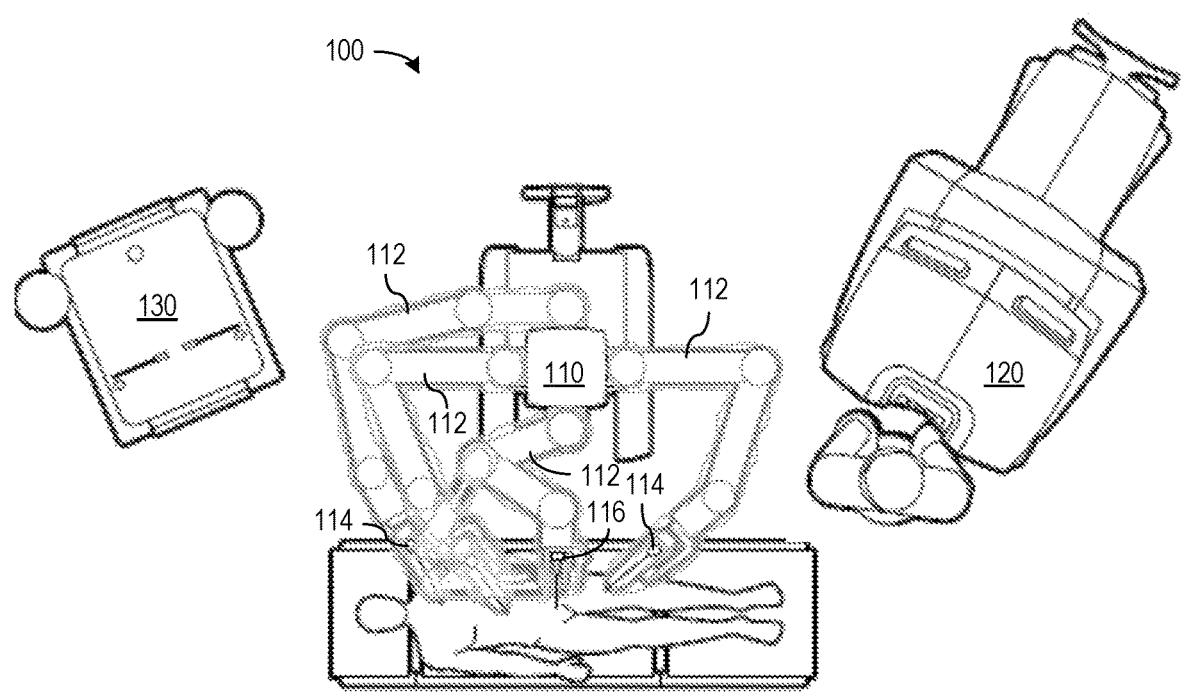
FIG. 1 shows an overhead view of one implementation of a medical system capable of detecting autonomous or other unintended movement of a master control.

FIG. 1 illustrates a robotic medical system 100, such as the da Vinci® Surgical System commercialized by Intuitive Surgical, Inc. (As used herein, the terms "robotic" or "robotically" and the like include teleoperation or telerobotic aspects.) Such medical systems allow an operator to move a surgical tool at least in part with the assistance of a computer (an arithmetic or logic unit coupled with a memory). System 100 includes a patient-side cart 110, a surgeon console 120, and an auxiliary equipment cart 130. Patient-side cart 110 includes multiple robotic arms 112. Subsystems such as interchangeable instruments 114 and cameras 116 can be mounted on arms 112. During a medical procedure, a cannula or other guide tube that may be part of arm 112 can be inserted through a small incision in a patient to guide the distal end of an instrument 114 to the work site inside the patient. Alternatively, a portion of the instrument may be introduced via a natural orifice, either with or without a cannula. An end effector, which may operate as a surgical tool such as a scalpel, forceps, a needle driver, a retractor, a cauterizer, or other device, is generally located at the distal end of each instrument 114 and may be used during a medical procedure performed at the work site.

Surgeon console 120 provides a control interface that a physician or other user can employ to control movement of arms 112, instruments 114, and camera 116. In particular, surgeon console 120 may include a stereoscopic viewer presenting a sensation of depth in the space in front of the distal tip of camera 116, as well as various buttons, switches, keys, foot pedals, joysticks, or similar devices that a user can manipulate to control patient-side cart 110 and particularly to use an end effector at the distal ends of instruments 114.

Auxiliary equipment cart 130 may control communications between surgeon console 120 and patient-side cart 110. In particular, cart 130 may include a computer system with suitable interface hardware, processing power, memory, and software to receive control signals from surgeon console 120 and to generate actuation signals sent to patient-side cart 110. In one specific implementation, cart 130 includes the central processing hardware for the integrated system, including reaction to system faults and display of messaging, and surgeon console 120 contains processing hardware including hardware executing instructions for detecting uncontrolled movement of a user operated controls. Alternatively, processing or other control hardware for a medical system such as system 100 may be located in patient-side cart 110, surgeon console 120, auxiliary equipment cart 130, or elsewhere.

Figure 2:
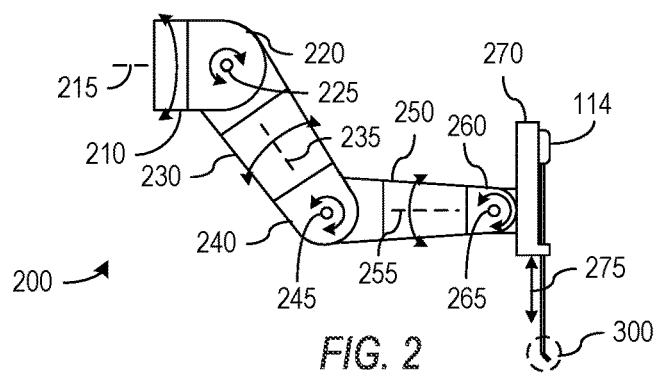
FIG. 2 schematically illustrates an implementation of a robotic arm that may form a portion of a slave device in a medical system.

All or portions of patient-side cart 110 may be considered a slave device under the control of a master device that forms all or parts of surgeon console 120. To illustrate one example of a slave device, FIG. 2 schematically shows an implementation of a lower arm portion 200 of one of robotic arms 112 of FIG. 1. Arm portion 200 in the illustrated embodiment includes a series of servomechanisms 210, 220, 230, 240, 250, 260, and 270, each of which provides a controlled degree of freedom of movement of arm portion 200. Each servomechanism 210, 220, 230, 240, 250, 260, or 270 generally includes a drive motor or other actuator that responds to an actuation signal by moving the servomechanism along its degree of freedom of motion. Each servomechanism 210, 220, 230, 240, 250, 260, or 270 may further include a sensing system that generates a measurement signal indicating a position or coordinate associated with the degree of freedom of the servomechanism, and the measurement signals may be used in feedback loops that control the positions of servomechanism 210, 220, 230, 240, 250, 260, and 270.

In the illustrated embodiment, servomechanism 210 may mount on patient-side cart 110 and particularly on an upper portion of an arm 112, which controls the pose of servomechanism 210. In response to an associated actuation signal, servomechanism 210 can rotate the distal portion of arm portion 200 including instrument 114 and servomechanisms 220, 230, 240, 250, 260, and 270 about an axis 215. Servomechanism 220 mounts on servomechanism 210 and includes an actuator or motor that in response to an associated actuation signal, rotates the distal portion of arm portion 200 including servomechanisms 230, 240, 250, 260, and 270 about an axis 225, which is perpendicular to axis 215. Servomechanism 230 mounts on servomechanism 220 and includes an actuator or motor that in response to an associated actuation signal, rotates the distal portion of arm portion 200 including servomechanisms 240, 250, 260, and 270 about an axis 235, which is perpendicular to axis 225. Servomechanism 240 mounts on servomechanism 230 and includes an actuator or motor that in response to an associated actuation signal, rotates the distal portion of arm portion 200 including servomechanisms 250, 260, and 270 about an axis 245, which is perpendicular to axis 235. Servomechanism 250 mounts on servomechanism 240 and includes an actuator or motor that in response to an associated actuation signal, rotates the distal portion of arm portion 200 including servomechanisms 260 and 270 about an axis 255, which is perpendicular to axis 245. Servomechanism 260 mounts on servomechanism 250 and includes an actuator or motor that in response to an associated actuation signal, rotates servomechanism 270 about an axis 265, which is perpendicular to axis 255. Servomechanism 270 includes a docking port for instrument 114 and may include an actuated slide for movement of instrument 114 along an insertion direction 275.

Figure 3:
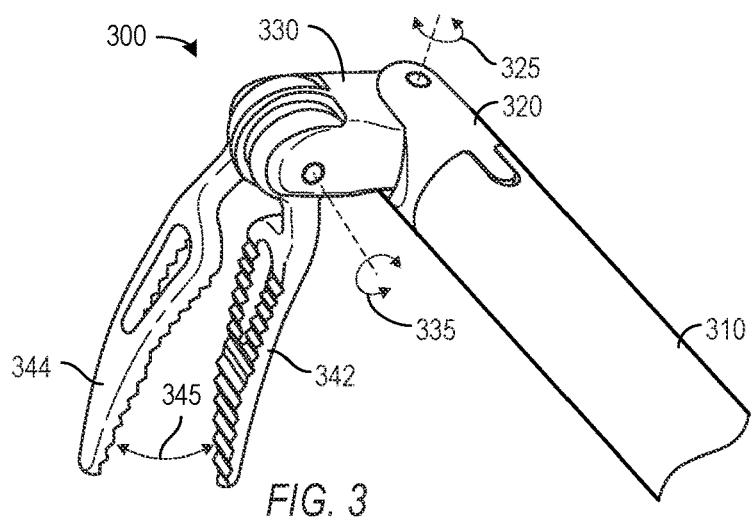
FIG. 3 shows an implementation of an end effector at the distal end of an instrument that may form a portion of a slave device in a medical system.

Instrument 114 typically provides further degrees of freedom of motion of a slave device that may be actuated using drive motors or other actuators in the docking port of servomechanism 270. FIG. 3, for example, illustrates an end effector 300 in an implementation in which instrument 114 operates as forceps. In the illustrated embodiment, end effector 300 is at the distal end of a main tube 310 of instrument 114 and includes a proximal clevis 320 mounted on the distal end of main tube 310, a distal clevis 330 rotatably mounted on proximal clevis 320, and jaws 342 and 344 rotatably mounted on distal clevis 330. The degrees of freedom of this specific embodiment of end effector 300 may be distinguished as rotation of distal clevis 330 about an axis 325 corresponding to a pin in proximal clevis 320, rotation of jaws 342 and 344 as a unit about an axis 335 corresponding to a pin in distal clevis 330, and angular separation 345 of jaw 342 from jaw 344. Each of the degrees of freedom of end effector 300 can be controlled using tendons, e.g., cables (not shown), that mechanically couple to one or more of mechanical elements 330, 342, and 344 and extend back through main tube 310 to a transmission or other backend mechanism of instrument 114 that couples to motors or other actuators in the docking port on arm 112.

Arm portion 200 of FIG. 2 and end effector 300 of FIG. 3 are merely examples of mechanical systems that may form portions of a slave device or medical system that may be operated as described further below. More generally, many different types of robotic arms and medical instruments are known or may be developed which can be employed in slave devices of medical systems that detect uncontrolled movement of the medical system. Further, slave devices in medical systems may include other types of actuated mechanical systems such as steerable guide tubes or catheters, articulated "snake" arms, or flexible linkages.

Figure 4:
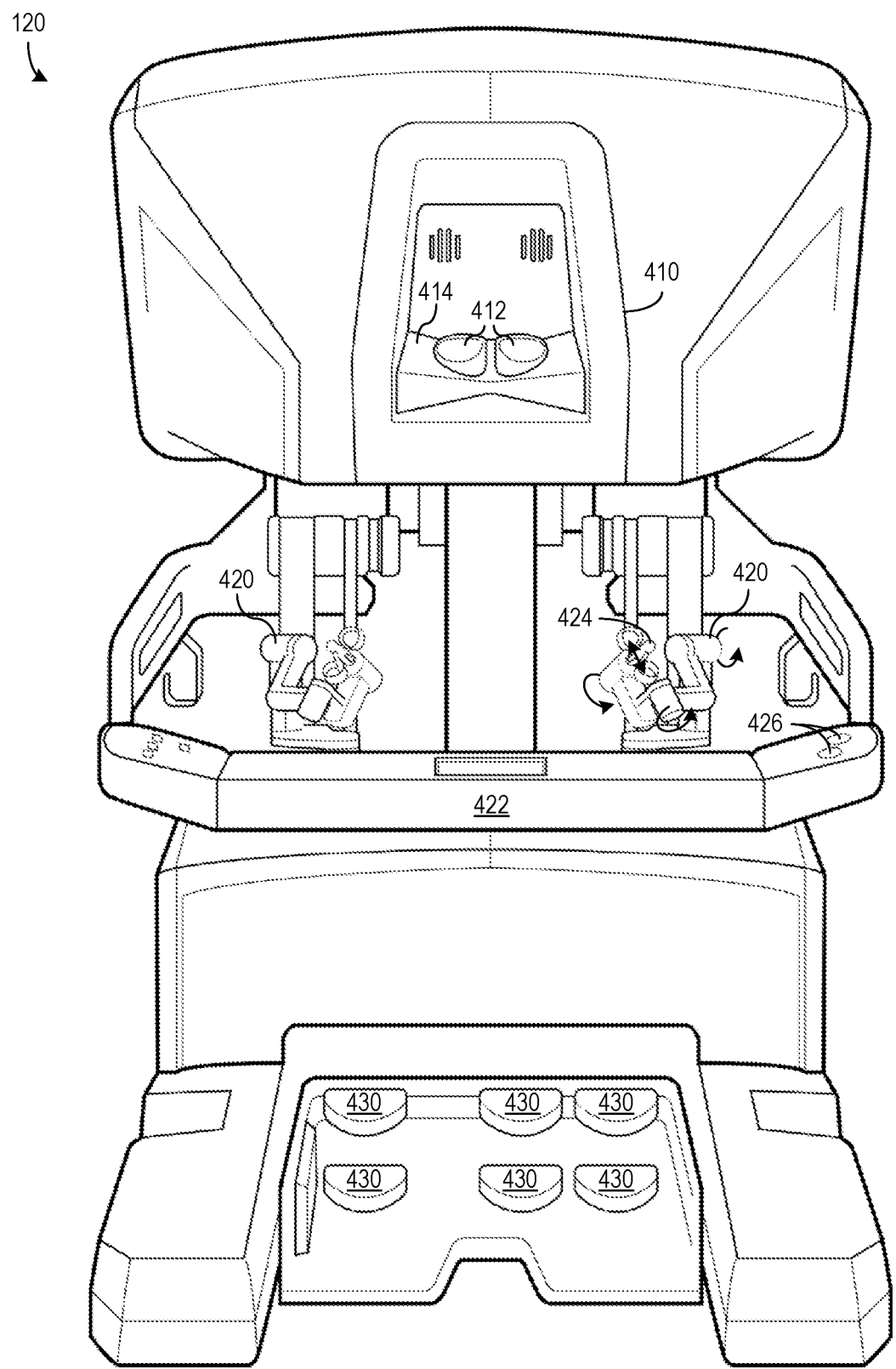
FIG. 4 shows an implementation of a surgeon console including master controls through which a surgeon can control a medical system.

FIG. 4 shows a front view of an exemplary embodiment of surgeon console 120. In the illustrated embodiment, surgeon console 120 includes view port 410, master controls 420, and foot pedals 430.

View port 410 may include a stereoscopic viewer 412 that displays a three-dimensional view from the point of view of a camera probe and may be used to view a work site during a medical procedure. When using surgeon console 120, a physician or other user typically sits in a chair in front of surgeon console 120, positions his or her head in view port 410 with eyes in front of viewer 412 and grips the master controls 420, one in each hand, while resting his or her forearms on a support 422. View port 410 may include a sensor 414 that senses when a user's head is in proper position for use of surgeon console 120. Sensors in controllers 420 or a processor in surgeon console 120 can generate control signals in response to the motion of master controls 420 or indicating the configuration of master controls 420 and the control signals may be used in generation of actuation signals that cause movement of one or more slave devices, e.g., one or more arms 112 or instruments 114 of FIG. 1. However, as a safety feature, movement of the slave devices may be disabled or limited if a sensing system, e.g., sensor 414, does not detect that a user is in position for proper use of surgeon console 120.

Each master control 420 has multiple degrees of freedom of motion that a user can manipulate by movement of a hand. In one specific implementation, the available degrees of freedom allow a user to manually control a tip 424 of each master controller 420 and particularly to manipulate: a location of tip 424, e.g., x, y, and z coordinates within a limited volume; an orientation of tip 424, e.g., pitch, yaw, and roll angles; and a grip angle and/or force for tip 424.

Figure 5:
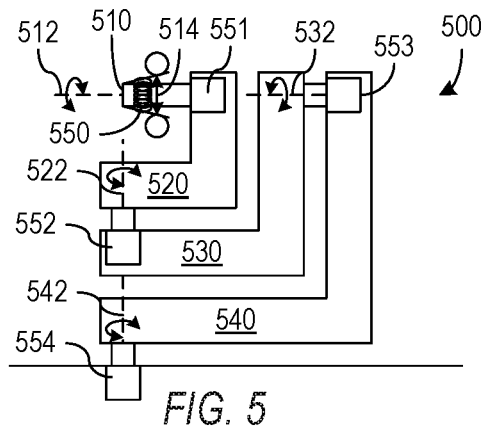
FIG. 5 schematically illustrates a portion of an implementation of a master control that can be manipulated using one hand to control multiple degrees of freedom of a slave device.

FIG. 5 schematically illustrates one implementation of a master control 500 having multiple joints that permit manipulation of the location, orientation, and grip angle of a control tip 510. Control tip 510 includes a grip angle sensor 550. For example, a user may insert fingers into loops movably mounted on control tip 510, and sensor 550 can measure a separation along axis 514 between the finger loops. Tip 510 is rotatably mounted on a link 520 so that a sensor 551 in link 520 can measure an angle of rotation of control tip 510 about an axis 512. The rotation of tip 510 about axis 512 may be the roll angle of tip 510. Link 520 is rotatably mounted on a link 530 to permit a sensor 552 to measure rotation of link 520 about an axis 522 that is perpendicular to axis 512. Link 530 is rotatably mounted on a link 540 to permit a sensor 553 to measure rotation of link 530 about an axis 532 that is perpendicular to axis 522. Link 540 may be rotatably mounted, and a sensor 554 can measure rotation of link 540 about an axis 542 that is perpendicular to axis 532. A computing system can determine the position, pitch, and yaw of control tip 510 from the measurements of rotation angles about axes 522, 532, and 542 and the known dimensions and geometries of links 520, 530, and 540. During a medical procedure, the location, orientation, and grip angle of tip 510 of master control 500 can be mapped to the corresponding location, orientation, and grip angle of a distal tip of an instrument or other slave device, and a control system can receive control signals from master control 500 that indicate the location, orientation, and grip angle of tip 510 and generate actuation signals for actuators that drive the corresponding location, orientation, and grip angle of the distal tip of a slave device.

Figure 6:
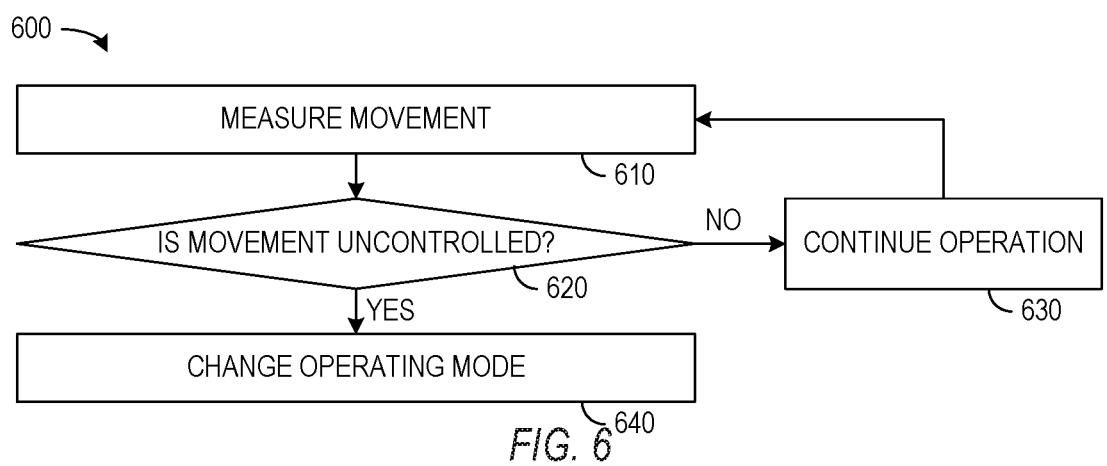
FIG. 6 is a flow diagram of one implementation of a process for operating a medical system and detecting uncontrolled movement.

FIG. 6 is a flow diagram of a process 600 that detects uncontrolled movement of a component of a robotic medical system. Process 600 begins with execution of a block 610 that measures movement of a manually operated component of a robotic medical system. The manually operated component generally has multiple degrees of freedom of motion, and in one implementation that manually operated component is a master control such as master control 500 of FIG. 5. Movement measurement block 610 generally includes detection or measurement of coordinates or changes in multiple degrees of freedom of the component, e.g., measurement of current rotation angles for multiple joints of a master control.

A decision block 620 determines whether the measured movement is uncontrolled (or likely to be uncontrolled). For example, decision block 620 may determine that movement is uncontrolled if movement occurs on specific gravity joints or degrees of freedom and no movement occurs on non-gravity joints. In particular, some joints of a master control can be identified as gravity joints and some joints of a master control can be classified as non-gravity joints. The classification of a joint may be independent of the current configuration of the master control or depend on the current configuration of the master control. For example, a joint may be classified as a gravity joint only if gravity can shift or move the joint in the current configuration of a master control. Alternatively, any joint that has the possibility of being moved by gravity can be classified as a gravity joint even if gravity would not shift the joint in its current pose. A joint may be classified as a non-gravity joint if in its current pose gravity would not shift the joint, or alternatively, a joint may be classified as a non-gravity joint only if gravity would not shift the joint in any of its possible configurations. If movement occurs on at least one non-gravity joint, decision block 620 determines that the movement is not uncontrolled, and a block 630 continues the current operation of the medical system, e.g., drives a slave device to follow the movement of the master control. If movement occurs on one or more of the gravity joints but none of the non-gravity joints, block 620 may consider the movement to be uncontrolled, and a block 640 can change the operating mode of the medical system, e.g., to shift the medical system to a locked mode or otherwise prevent movement of the master or prevent movement of the slave in response to the movement of the master.

Process 600 may also be applied in robotic systems in which a user is manipulating a component other than a master control. For example, a medical system such as system 100 of FIG. 1 may implement a clutch mode. Clutch mode may be used when a portion of slave, e.g., a slave arm 112, is not being controlled by a closed feedback loop with the master control in surgeon console 120, but rather is floating or is otherwise free to move in space. Clutch mode may allow a user such as a surgical side assistant to manually manipulate and reposition an arm 112 relative to a patient or directly make some other clinically appropriate adjustment of the arm 112. When operating in clutch mode, a control system can perform block 610 to measure movements in multiple degrees of freedom of arm 112, and decision block 620 can evaluate relationships between the measured movements to determine whether movement of the arm 112 is uncontrolled. Clutch mode and manual movement of the arm 112 can continue through block 630 as long as the movement is controlled. However, if the slave arm 112 has some degrees of freedom which are affected by gravity and some degrees of freedom that are not, decision block 620 can apply the same logic as described above to determine whether a user is manually controlling an arm 112 while the arm 112 is operated in the clutch mode. If some of the gravity axes move more than a threshold but there is not corresponding motion of the non-gravity axes, block 640 could pull the arm 112 out of clutch mode and stop or limit further manual movement.

Figure 7A:
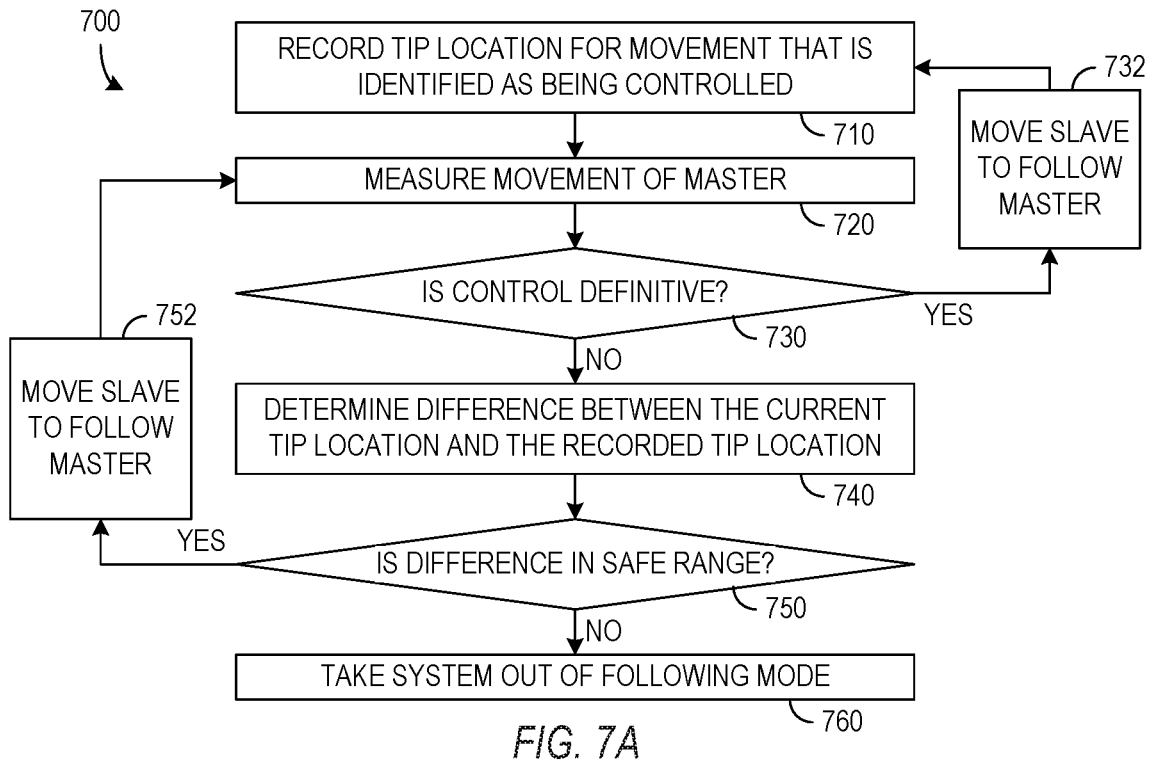
FIGS. 7A and 7B are flow diagrams of some other implementations of processes for operating a medical system and detecting uncontrolled motions of manually manipulated components of the medical system.

FIG. 7A is a flow diagram of a process 700 that detects uncontrolled movement of a master by tracking how far the tip of the master has moved since the last definitive input from the user. Definitive input in this context means that the detected movement satisfies conditions that are accepted as definitively indicating that a user controlled the movement. In general, a determination of whether movement is definitively controlled may depend on the specific master control or component being used. However, one example of definitive input may be any movement including a measured velocity or change in the roll angle of control tip 510 of FIG. 5, if the master is such that gravity or bumping of the master cannot or is unlikely to rotate tip 510. Another example of definitive input may be a measured separation along the grip axis 514 if the measure separation indicates that the user is holding tip 510 partially closed against a restoring spring force. More generally, definitive input can be logically or mathematically identified by a control system through evaluation of relationships for or among the positions, orientations, velocities, or accelerations of degrees of freedom of a master control, particularly for relationships that are indicative of input from the user's hand.

Process 700 begins with a block 710 that records the location of the tip of a master when movement of the master is identified as being definitive input. The recording of the tip position in block 710 may initially occur when a user initiates a "following" mode of a medical system in which the slave follows the movement of the master. After some time, a block 720 measures movement or a new configuration of the master, e.g., for master 500 of FIG. 5 measures angles or determines changes in angles respectively associated with one or more rotation axes 512, 522, 532, and 542 or measures separation or a change in separation along axis 514.

A decision block 730 determines whether the movement just measured definitively indicates control, i.e., corresponds to definitive input. For example, a change in the roll angle, e.g., a change in rotation angle of tip 510 about axis 512, may indicate controlled movement or definitive input. Definitive input could also be indicated by a measured grip, e.g., a separation along axis 514 indicates an external force is being applied to tip 510. Other indicators of definitive input are possible. If the movement is determined to be definitive input, a control system performs a block 732 to generate actuation signals that cause the slave to follow the movement of the master, and a new tip location for the last definitive movement is recorded by execution of block 710.

If block 730 fails to determine that the tip movement just measured is definitive input, the movement of the master may or may not be under the control of a user. However, if the tip of the master remains within a safe range, then following can continue. Block 740 then determines the difference between the current tip location and the tip location recorded when tip movement last indicated definitive input, and a decision block 750 determines whether the movement is in a safe range. If the difference is in the safe range, the control system performs a block 752 to generate actuation signals that cause the slave to follow the movement of the master, and the next movement of the master is measured in block 720. If the difference is outside the safe range, the slave is not permitted to follow the movement of the master, and a block 760 may take the medical system out of following mode. When taken out of following mode, movement of the slave is prevented until a user reestablishes the following mode, and the user may be instructed to perform a deliberate action such as squeezing the grips in order to return the medical system to following mode.

The safe range used in decision step 750 in general may depend on many factors, such as the pose or state of the medical system as a whole, the type of instrument or instruments currently being controlled, the current pose of the instrument(s), which degrees of freedom of the master are moved, the surgeon's operating speed, and dimensions of the work site. In an extreme case, the safe range has size zero so that no movement of the slave is permitted except when movement of the master is determined to be definitive input. However, even when uncontrolled movement of the master occurs, for example, when a user temporarily lets go of the master but the master does not move, the uncontrolled movement of the master is not necessarily a hazardous situation. The safe range can provide the thresholds based on how far the tip of the master has travelled, either linearly, or in rotation, or combined linear and rotation, for detection of unsafe uncontrolled movement. A user may thus be able to safely recover and continue in following mode after an uncontrolled movement of the master, without the system entering a safe mode and therefore without requiring the user to reenter the following mode. The time consuming process of repeatedly demonstrating control of the master or otherwise returning the medical system to following mode can thus safely be avoided.

Figure 7B:
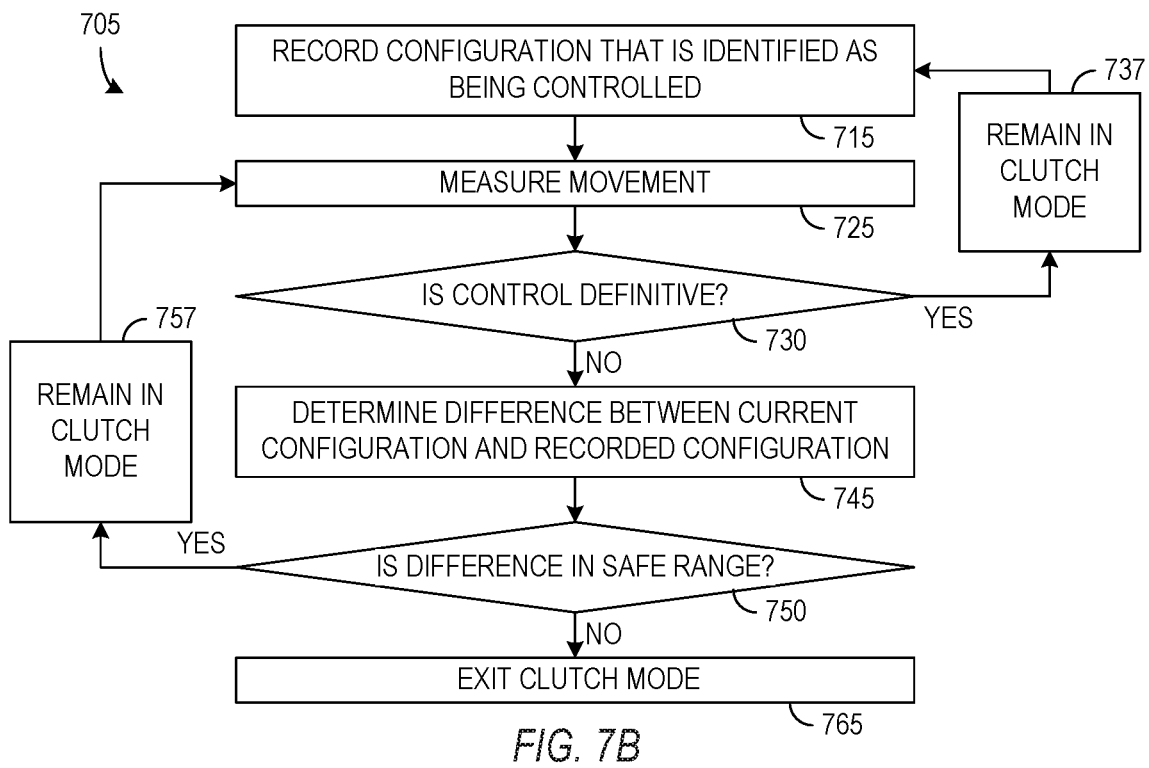

Process 700 as described above analyzes movement of a master and limits movement of a slave device when the movement of a master is uncontrolled. Similar processes can also be employed when other components of a robotic medical system may be manually manipulated. For example, FIG. 7B is a flow diagram of a process 705 for operating a medical system and detecting uncontrolled movement of a slave component that might be manually manipulated. For example, the medical system may place a component such as a robotic arm into a clutch mode in which a user may directly and manually manipulate the arm. Process 705 begins in block 715 by recording a configuration in which a component is free to be manipulated (i.e., in clutch mode) and is definitively under user control. Movement of the component can be subsequently measured (block 725) and a decision block 730 can determine if the component is then definitively under user control. If so, the component can remain in clutch mode (block 737) and a new configuration can be recorded (block 715). If decision block 730 determines that the component is not definitively under control, block 745 can determine the change in configuration, and block 750 can evaluate whether the component is in a safe range. If so, the component may remain in clutch mode (block 757). If not, the system can exit clutch mode (block 765) for the component.

Figure 8:
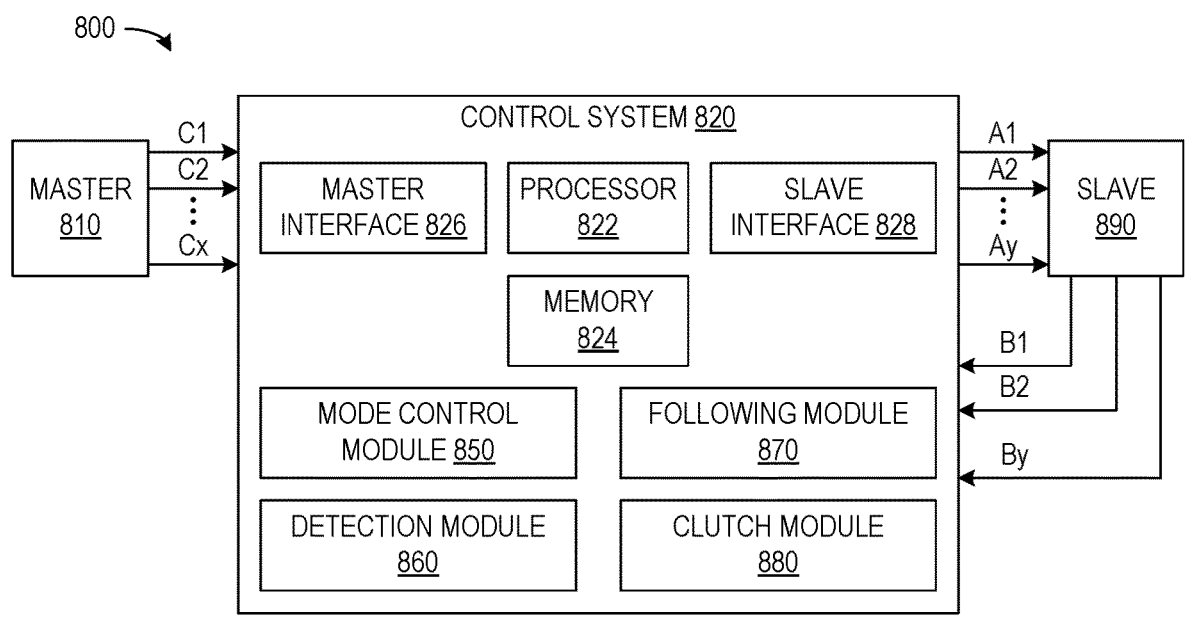
FIG. 8 is a block diagram of an implementation of a medical system including detection of autonomous or unintended movement.

FIG. 8 is a block diagram of a master-slave system 800 in accordance with an embodiment of the invention. System 800 includes a master device 810 that a human user may manipulate in order to control a slave device 890. In one specific implementation, master device 810 may be similar or identical to master control 500 of FIG. 5, but more generally, master 810 can be any type of device having multiple degrees of freedom of movement. Master device 810 generates control signals C1 to Cx indicating states or changes of its degrees of freedom.

A control system 820 receives control signals C1 to Cx and generates actuation signals A1 to Ay, which are sent to slave 890. Control system 820 may be a computing system such as a general purpose computer and may include conventional components such as a processor 822, memory 824, and interface hardware 826 and 828 for communication with master device 810 and slave device 890.

Control system 820 in the illustrated embodiment includes a mode control module 850, a detection module 860, a following module 870, and a clutch module 880. As used herein, the term "module" refers to a combination of hardware (e.g., a processor such as an integrated circuit or other circuitry) and software (e.g., machine or processor executable instructions, commands, or code such as firmware, programming, or object code). A combination of hardware and software includes hardware only (i.e., a hardware element with no software elements), software hosted at hardware (e.g., software that is stored at a memory and executed or interpreted by or at a processor), or hardware and software hosted at hardware.

Mode control module 850 detects when a human user initiates an operating mode such as a following mode or a clutch mode of the medical system and may switch the operating mode automatically, for example, when detection module 860 detects potentially unsafe uncontrolled movement in master-slave system 800. In the following mode, control system 820 uses following module 870, which receives control signals C1 to Cx and generates actuation signals A1 to Ay that cause slave device 890 to follow the movement of master device 810. Detection module 860 may simultaneously monitor control signals C1 to Cx and detect any unsafe uncontrolled movement of master 810. For example, in an implementation described above, mode control module 850 may activate following mode operation if sensor 414 indicates that a user is in proper position for use of master control 420 and the control signals indicate the human operator has depressed a grip sensor and rotate a roll sensor in the master control and may disable following mode if detection module indicates an unsafe uncontrolled movement of master 810.

Following module 870 may perform the calculation necessary to generate actuation signals A1 to Ay that cause slave 890 to follow the movements of master 810, e.g., so that the movements of slave 890 correspond to a mapping of the movements of master 810. Following module 870 can be implemented using conventional techniques. Detection module 860 may implement process 600 of FIG. 6 and if unsafe, uncontrolled movement of master 810 is detected, detection module 860 may inform mode control module 850 or directly prevent following module 870 from generating actuation signals A1 to Ay that move slave 890.

A clutch module 880 may be employed for a clutch mode of system 800. In the clutch mode, movement of one or more degree of freedom of master 810 has no effect on the movement of one or more components of slave 890. Clutch mode may be used when a portion of slave 890, e.g., a slave arm, is not being controlled by a closed feedback loop with master 810, but rather is floating in space and may be manually moved. For clutch mode, clutch module 880 may allow servo systems in slave to be freewheeling or may generate actuation signals A1 to Ay such that motors in an arm support the expected weight of the arm against gravity, but brakes in the arm are not engaged and instead permit manual movement of the arm. Clutch mode may allow a surgical side assistant to easily manipulate and reposition an arm or other slave component relative to a patient or directly make some other clinically appropriate adjustment of the arm or slave component. Sensor signals B1 to By from slave 890, which may be used in a feedback loop control in following mode, can be analyzed by detection module 860 to detect uncontrolled movement of slave 890. If analysis of signals B1 to By indicates uncontrolled or unsafe movement of slave 890, detection module 860 or mode control module 850 can take system 800 out of clutch mode and may apply brakes in slave 890 to prevent further manual or uncontrolled movement of slave 890.

Some embodiments of the above invention can be implemented in a computer-readable media, e.g., a non-transient media, such as an optical or magnetic disk, a memory card, or other solid state storage containing instructions that a computing device can execute to perform specific processes that are described herein. Such media may further be or be contained in a server or other device connected to a network such as the Internet that provides for the downloading of data and executable instructions.

Although particular implementations have been disclosed, these implementations are only examples and should not be taken as limitations. Various adaptations and combinations of features of the implementations disclosed are within the scope of the following claims.

What is claimed is:
1. A system comprising:
a manually movable input control configured to generate one or more signals when a movement of one or more mechanical degrees of freedom of the input control is detected; and
a control module coupled to the input control;
wherein the control module is configured to:
determine whether a distance of a movement of the input control relative to a position of the input control when a last definitive movement of the input control was detected is greater than a threshold distance, and command the system to switch from an operating mode to a safe mode in response to determining that the distance of the movement of the input control relative to the position of the input control when the last definitive movement of the input control was detected is greater than the threshold distance;

wherein:
the operating mode comprises a following mode in which an instrument moves in response to movement of the input control, and
the safe mode comprises a mode in which the instrument does not move in response to movement of the input control.

2. The system of claim 1, wherein the threshold distance depends on an operating speed of the input control.

3. The system of claim 1, wherein the threshold distance depends on a type of an instrument being moved.

4. The system of claim 1, wherein the threshold distance depends on at least one criterion selected from a group consisting of: a current pose of the instrument, a degree of freedom of the input control that is moved, and a dimension of a worksite in which the instrument is located.

5. The system of claim 1, wherein the threshold distance includes one or more thresholds based on how far a tip of the input control has travelled.

6. The system of claim 1, wherein the control module is further configured to return the system to the operating mode in response to detecting a deliberate action performed on the input control.

7. The system of claim 6, wherein the deliberate action is a closing of grips of the input control.

8. The system of claim 1, wherein the control module is further configured to:
determine whether a first mechanical degree of freedom of the input control has moved, wherein the first mechanical degree of freedom is affected by gravity;
determine whether a second mechanical degree of freedom has not moved, wherein the second mechanical degree of freedom is not affected by gravity; and
command the system to switch from the operating mode to the safe mode in response to determining that the first mechanical degree of freedom has moved and that the second mechanical degree of freedom has not moved.

9. The system of claim 1, wherein the control module is further configured to:
determine whether the one or more signals indicate that no definitive movement has occurred on the input control, wherein the definitive movement comprises at least one input selected from a group consisting of: a change in a roll angle of the input control, and a change in a grip separation of the input control; and
command the system to switch from the operating mode to the safe mode in response to determining that no definitive movement has occurred on the input control.

10. The system of claim 1, wherein the control module is further configured to:
determine whether the one or more signals indicate that a first mechanical degree of freedom of the input control has not moved, wherein the first mechanical degree is not affected by gravity; and
command the system to switch from the operating mode to the safe mode in response to determining that the first mechanical degree of freedom has not moved.

11. A method comprising:
detecting a movement of a manually movable input control of a device, the input control having one or more movable mechanical degrees of freedom;
determining whether a distance of the movement of the input control relative to a position of the input control when a last definitive movement of the input control was detected is greater than a threshold distance; and
commanding the device to switch from an operating mode to a safe mode in response to determining that the distance of the movement of the input control relative to the position of the input control when the last definitive movement of the input control was detected is greater than the threshold distance;

wherein:
the operating mode comprises a following mode in which an instrument moves in response to movement of the input control, and
the safe mode comprises a mode in which the instrument does not move in response to movement of the input control.

12. The method of claim 11, wherein the threshold distance depends on an operating speed of the input control.

13. The method of claim 11, wherein the threshold distance depends on a type of the instrument.

14. The method of claim 11, wherein the threshold distance depends on at least one criterion selected from a group consisting of: a current pose of the instrument, a degree of freedom of the input control that is moved, and a dimension of a worksite in which the instrument is located.

15. The method of claim 11, wherein the threshold distance includes one or more thresholds based on how far a tip of the input control has travelled.

16. The method of claim 11, further comprising:
returning the device to the operating mode in response to detecting a closing of grips of the input control.

17. A non-transitory computer-readable media containing instructions that, when executed by a processor, are configured to cause a device to perform a method comprising:
detecting a movement of a manually movable input control of a device, the input control having one or more movable mechanical degrees of freedom;
determining whether a distance of the movement of the input control relative to a position of the input control when a last definitive movement of the input control was detected is greater than a threshold; and
commanding the device to switch from an operating mode to a safe mode in response to determining that the distance of the movement of the input control relative to the position of the input control when the last definitive movement of the input control was detected is greater than the threshold distance;

wherein:
the operating mode comprises a following mode in which an instrument moves in response to movement of the input control, and
the safe mode comprises a mode in which the instrument does not move in response to movement of the input control.

18. The non-transitory computer-readable media of claim 17, wherein the threshold distance depends on an operating speed of the input control or a type of the instrument.

19. The non-transitory computer-readable media of claim 17, wherein the threshold distance depends on at least one criterion selected from a group consisting of: a current pose of the instrument, a degree of freedom of the input control that is moved, and a dimension of a worksite in which the instrument is located.

20. The non-transitory computer-readable media of claim 17, wherein the threshold distance includes one or more thresholds based on how far a tip of the input control has travelled.

* * * * *

UNITED STATES PATENT AND TRADEMARK OFFICE
CERTIFICATE OF CORRECTION

PATENT NO. : 11,607,281 B2
APPLICATION NO. : 16/824575
DATED : March 21, 2023
INVENTOR(S) : Michael Turner It is certified that error appears in the above-identified patent and that said Letters Patent is hereby corrected as shown below:

On the Title Page

(63) Related U.S. Application Data:
Please delete "Continuation of application No. 15/503,358, filed as application No. PCT/US2015/044590 on Aug. 11, 2015, now Pat. No. 10,646,291." and insert --Continuation of application No. 15/503,358, filed on Feb. 10, 2017, now Pat. No. 10,646,291, which is a 371 of application No. PCT/US2015/044590, filed on Aug. 11, 2015.--;

In the Claims

Column 12, Claim 17, Line 44, please insert --distance-- after threshold.

Signed and Sealed this
Eighteenth Day of April, 2023

Katherine Kelly Vidal
*Director of the United States Patent and Trademark Office*